United States Patent
Penton Rol et al.

(10) Patent No.: US 9,518,085 B2
(45) Date of Patent: Dec. 13, 2016

(54) COMPOUNDS AND PHARMACEUTICAL COMBINATIONS FOR THE TREATMENT OF NEURODEGENERATIVE AND ISCHEMIC BRAIN DISEASES

(75) Inventors: Giselle Penton Rol, La Habana (CU); Alexey Llopiz Arzuaga, Granma (CU); Javier Marin Prida, La Habana (CU); Eduardo Penton Arias, La Habana (CU); Efrain Rodriguez Jimenez, La Habana (CU); Alexis Musacchio Lasa, Artemisa (CU); Vladimir Armando Besada Perez, La Habana (CU); Gilberto Lazaro Pardo Andreu, La Habana (CU); Luis Javier Gonzalez Lopez, La Habana (CU); Nancy Pavon Fuentes, La Habana (CU); Gerardo Enrique Guillen Nieto, La Habana (CU); Pedro Antonio Lopez Saura, La Habana (CU)

(73) Assignee: CENTRO DE INGENIERÍA GENÉTICA Y BIOTECHNOLOGÍA, La Habana (CU)

( * ) Notice: Subject to any disclaimer, the term of this patent is extended or adjusted under 35 U.S.C. 154(b) by 79 days.

(21) Appl. No.: 14/127,369

(22) PCT Filed: Jun. 29, 2012

(86) PCT No.: PCT/CU2012/000003
§ 371 (c)(1),
(2), (4) Date: Aug. 14, 2014

(87) PCT Pub. No.: WO2013/004203
PCT Pub. Date: Jan. 10, 2013

(65) Prior Publication Data
US 2014/0356319 A1    Dec. 4, 2014

(30) Foreign Application Priority Data

Jul. 1, 2011  (CU) ................... 2011/0146

(51) Int. Cl.
| | |
|---|---|
| C07K 7/06 | (2006.01) |
| C07K 5/08 | (2006.01) |
| A61K 38/00 | (2006.01) |
| C07K 5/10 | (2006.01) |
| C07K 5/083 | (2006.01) |
| C07K 5/103 | (2006.01) |
| A61K 38/06 | (2006.01) |
| A61K 38/07 | (2006.01) |
| A61K 38/18 | (2006.01) |
| A61K 38/20 | (2006.01) |
| A61K 38/21 | (2006.01) |
| A61K 38/25 | (2006.01) |
| A61K 38/08 | (2006.01) |

(52) U.S. Cl.
CPC ............. C07K 7/06 (2013.01); A61K 38/06 (2013.01); A61K 38/07 (2013.01); A61K 38/08 (2013.01); A61K 38/1816 (2013.01); A61K 38/2013 (2013.01); A61K 38/21 (2013.01); A61K 38/212 (2013.01); A61K 38/215 (2013.01); A61K 38/25 (2013.01); C07K 5/08 (2013.01); C07K 5/081 (2013.01); C07K 5/10 (2013.01); C07K 5/1008 (2013.01); A61K 38/00 (2013.01)

(58) Field of Classification Search
None
See application file for complete search history.

(56) References Cited

U.S. PATENT DOCUMENTS

| | | | | |
|---|---|---|---|---|
| 2004/0110938 A1* | 6/2004 | Parekh | ................. | C07K 14/705 536/23.5 |
| 2006/0198821 A1* | 9/2006 | Jalkanen | ............ | A61K 31/7076 424/85.2 |
| 2009/0280087 A1* | 11/2009 | Penton Rol | ............ | A61K 31/40 424/85.7 |
| 2010/0172971 A1* | 7/2010 | McCarty | ................ | A61K 31/40 424/456 |

OTHER PUBLICATIONS

Arciero 1988 "in vitro attachment of bilins to apophycocyanin" JBC 263(34):18350-18357.*
Kim 2015"ethics of genetic and biomarker test disclosures in neurodegenerative disease prevention trials" neurology 84:1488-1494.*
Medscape 2015 "Down syndrome treatment and management" accessed from medscape.com on Sep. 14, 2015.*
Rafii 2009 "Recent developments in Alzheimer's disease therapeutics" BMC medicine 7:7.*

* cited by examiner

*Primary Examiner* — Adam M Weidner
(74) *Attorney, Agent, or Firm* — Hoffmann & Baron, LLP

(57) ABSTRACT

The present invention describes peptides comprising phycocyanobilin (PCB), as well as the medical use of said peptides and that of PCB, due to the neuroprotector and/or neuroregenerative effects identified for them. Furthermore, pharmaceutical combinations of said peptides and of PCB with proteins or other peptides with synergic effect justify their use for ischemic or neurodegenerative CNS disease treatment.

7 Claims, 6 Drawing Sheets

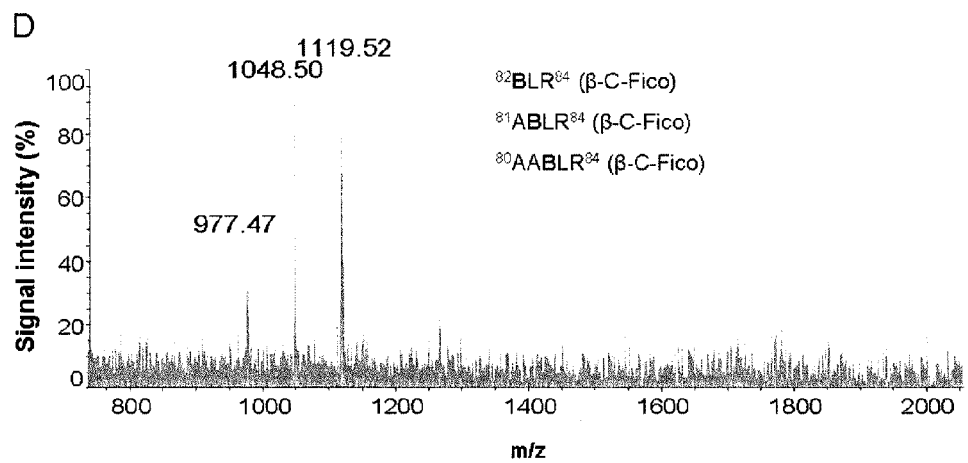
Figure 2
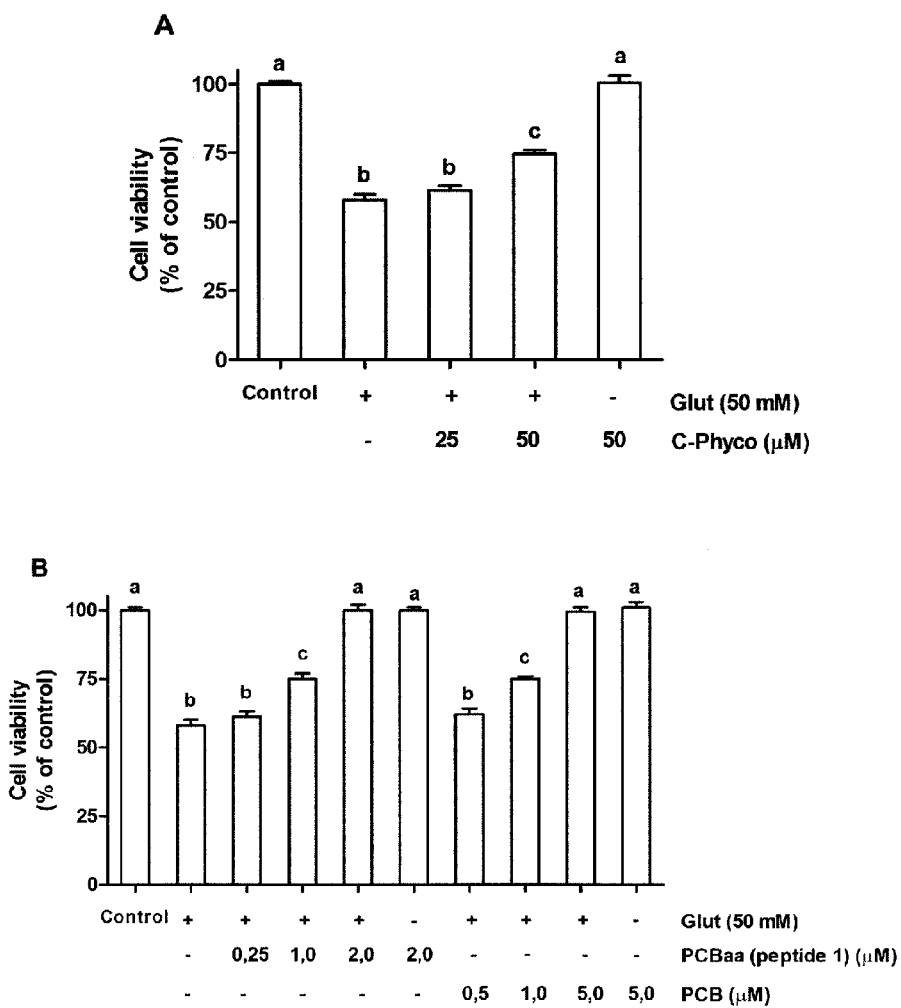

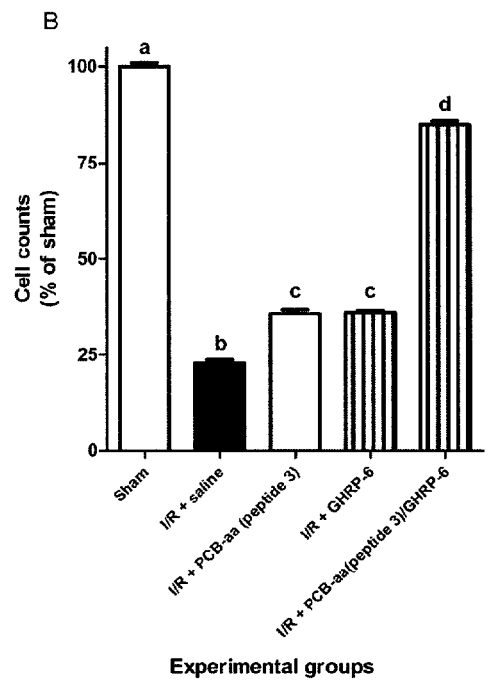
Figure 9
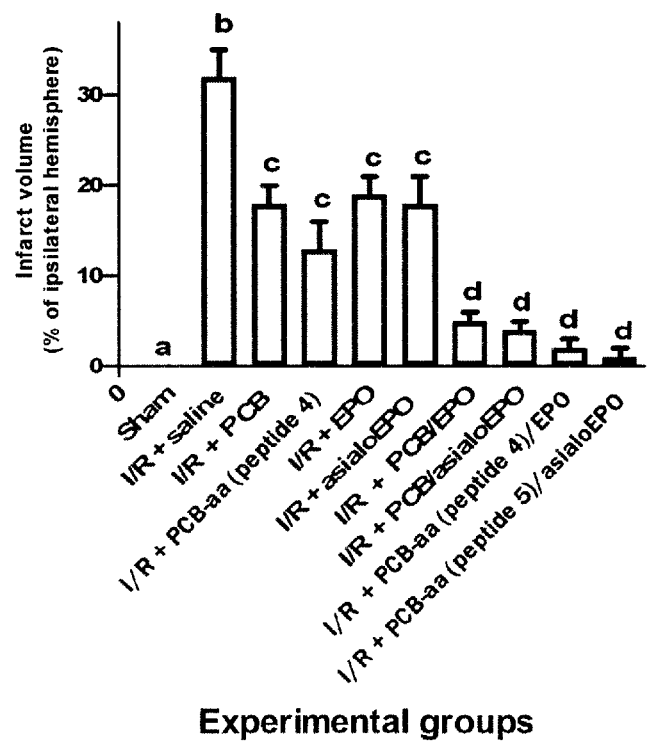

```
                        SEQUENCE LISTING

<160> NUMBER OF SEQ ID NOS: 5

<210> SEQ ID NO 1
<211> LENGTH: 6
<212> TYPE: PRT
<213> ORGANISM: Spirulina platensis
<220> FEATURE:
<221> NAME/KEY: PEPTIDE
<222> LOCATION: (4)..(4)
<223> OTHER INFORMATION: Cysteine residue covalently attached to
      phycocyanobilin by a thioether linkage

<400> SEQUENCE: 1

Met Ala Ala Cys Leu Arg
1               5

<210> SEQ ID NO 2
<211> LENGTH: 3
<212> TYPE: PRT
<213> ORGANISM: Spirulina platensis
<220> FEATURE:
<221> NAME/KEY: PEPTIDE
<222> LOCATION: (1)..(1)
<223> OTHER INFORMATION: Cysteine residue covalently attached to
      phycocyanobilin by a thioether linkage

<400> SEQUENCE: 2

Cys Ala Arg
1

<210> SEQ ID NO 3
<211> LENGTH: 5
<212> TYPE: PRT
<213> ORGANISM: Spirulina platensis
<220> FEATURE:
<221> NAME/KEY: PEPTIDE
<222> LOCATION: (3)..(3)
<223> OTHER INFORMATION: Cysteine residue covalently attached to
      phycocyanobilin by a thioether linkage

<400> SEQUENCE: 3

Ala Ala Cys Leu Arg
1               5

<210> SEQ ID NO 4
<211> LENGTH: 3
<212> TYPE: PRT
<213> ORGANISM: Spirulina platensis
<220> FEATURE:
<221> NAME/KEY: PEPTIDE
<222> LOCATION: (1)..(1)
<223> OTHER INFORMATION: Cysteine residue covalently attached to
      phycocyanobilin by a thioether linkage

<400> SEQUENCE: 4

Cys Leu Arg
1

<210> SEQ ID NO 5
<211> LENGTH: 4
<212> TYPE: PRT
<213> ORGANISM: Spirulina platensis
<220> FEATURE:
<221> NAME/KEY: PEPTIDE
```

```
<222> LOCATION: (2)..(2)
<223> OTHER INFORMATION: Cysteine residue covalently attached to
      phycocyanobilin by a thioether linkage

<400> SEQUENCE: 5

Ala Cys Leu Arg
1
```

COMPOUNDS AND PHARMACEUTICAL COMBINATIONS FOR THE TREATMENT OF NEURODEGENERATIVE AND ISCHEMIC BRAIN DISEASES

CLAIM OF PRIORITY

This application is the U.S. National Phase of, and Applicants claim priority from, International Application Number PCT/CU2012/000003 filed Jun. 29, 2012 and Cuban Patent Application No. CU 2011/0146 filed Jul. 1, 2011, which are incorporated herein by reference.

TECHNICAL FIELD

The present invention is related to Biological Sciences, Pharmacology, Neurobiology, Biotechnology and Medical Sciences, specially Neurology and Internal Medicine. It is related, in general, with the generation of therapies for Central Nervous System (CNS) diseases which proceed or derive from ischemic, inflammatory and/or neurodegenerative damage.

The invention is based on the use of C-Phycocyanin (C-Phyco) derivatives or parts of this molecule, presenting pyrrolic rings in their structure, for cerebrovascular disease treatment, characterized by tissue hypoxia and diseases with inflammatory and neurodegenerative components. They also include the pharmaceutical combinations of said compounds with other biomolecules, which are administered both prophylactically and therapeutically.

PRIOR STATE OF THE ART

The treatment of cerebrovascular, demyelinating and neurodegenerative diseases represents a new frontier in the field of Neurosciences. Cerebrovascular accidents (CVA) affect around 5% of the World population aged 65 years old or more and can produce serious physical disabilities in affected individuals (World Health Organization: Statistical Information System. World Health Organization, 2004). More than 90% of deaths occur in persons aged 50 years old or more and approximately 15% to 30% of surviving patients present some type of sequel (Buergo-Zuaznabar M A, et al. Revista Electrónica de las Ciencias Médicas en Cienfuegos: 2-22; Miranda Q J A. Cerebrovascular Diseases, 2004; 1: 17-21; Rosamond W, et al. Circulation. 2007:169-171).

Around 80% of CVA, according to the World Health Organization (WHO) data, are of the ischemic type which have their origin in the acute occlusion of one of the main brain arteries by a thrombus or an embolus (World Health Organization: Statistical Information System. World Health Organization, 2004), which originates a reduction of perfusion of the region irrigated by that artery.

Neuroprotection is a prophylactic and therapeutic treatment strategy, with the fundamental objective of preventing the pathological loss of neurons occurring in CNS diseases, such as during ischemia. Neuroregeneration has the fundamental objective of reverting the damage occurred in neuroinflammatory and neurodegenerative diseases such as Multiple Sclerosis (MS).

The main objective of brain schemia treatment are: (1) to reduce the size of the ischemic zone, limiting its possible extension to the adjacent area; (2) to limit the progressive advance of cell death to the recoverable zone of penumbra within an adequate therapeutic window (Muhammad S H A S. Eur Neurol. 2008; 59:4-14).

The new neuroprotector and/or neuroregenerator therapeutic agent candidates, must block and/or attenuate the cell metabolic biochemical processes leading to progressive brain damage during and after the ischemic event. Furthermore, they must cover a broad spectrum of possible pharmacological targets within the brain damage pathogenic mechanism (Ovbiagele B, et al. Curr Treat Options Cardiovasc Med. 2003; 5:441-449).

There is evidence of compounds extracted from natural sources with neuroprotector and/or neuroregenerator effects in ischemic type disorders, as well as in neurodegenerative diseases. Several studies indicate that natural and synthetic cannabinoids are able to produce neuroprotector effects in brain ischemia (Mauler F, et al. J Pharmacol Exp Ther. 2002; 302(1): 359-68; Iadecola C. Curr Opin Neurol. 2001; 14: 89-94; Sinor A D, et al. Neurosci Lett. 2000; 278(3): 157-60), multiple sclerosis (Baker D, Pryce G, Croxford J L, Brown P, Pertwee R G, et al. Nature. 2000; 404(6773): 84-87), Huntington's disease (Lastres-Becker I, et al. Brain Res. 2002; 929(2): 236-42) and in Parkinson's disease (Lange J M, et al. DDT. 2005; 10(10): 693-702) by means of different antioxidant mechanisms and excitotoxicity inhibition by decreasing and blocking the release of amino acids and inflammation mediators.

In spite of this, there are important adverse effects associated to cannabinoids depending, to a large extent, on dose dependence, on the concentration of cannabinoid compounds in each dose, on the experience of the consumer and the time of consumption.

Acute effects have been reported, to a large extent due to the anticholinergic effects of cannabinoids including: mouth dryness, eye reddening, blurry vision, blood pressure decrease, increase of heart rate, decrease of reaction capacity, increase of perceived sensations, loss of coordination and slowdown of psychomotor pace. Chronic effects have also been reported, such as: immune system dysfunction with a possible increase of cancer incidence which surpasses, in the case of lung cancer, the incidence rate for tobacco consumers. Increase of the risk of acute myocardium infarct, infertility, liver fibrosis in hepatitis patients and the possible risk of increase of epilepsy is still under debate for cannabinoid consumers; and some psychic effects, given by the fact that cannabis consumption may trigger alterations of perception such as hallucinations, distortion of time-space perception, or depersonalization and/or derealization phenomena. Anxiety crises, psychotic type acute crises, euphoria, excessive loquacity, as well as cognitive dysfunction such as short-term memory loss or slowness of thinking, non-reversible cognitive alterations, worsening of previous psychiatric problems, increase of risk of schizophrenia. Alterations of the mood have also been described (depressive and/or maniac), social marginality, as well as dependence to cannabis consumption, which in some cases initiates the consumption of other drugs. It must be emphasized that cannabis consumption during pregnancy may derive in cognitive and psychopathological alterations of the offspring during adolescence.

C-phyco is a biliprotein found in some blue-green algae such as *Spirulina platensis*, which is often used as a dietary supplement in many countries with well proven nutritional and cytoprotective properties (Bockow B I. U.S. patent Ser. No. 05/709,855 (1998); Kay, R. A. Crit. Rev. Food Sci. Nutr. 1991; 30: 555-573; Gonzalez De R C, et al. Life Sci. 1993; 53: 57-61).

A large part of the studies with C-Phyco have had the purpose of demonstrating antioxidant properties. The C-Phyco free radical sequestrating action was demonstrated by an assay on: (1) chemo-luminescence, and (2) of inhibition of 2-deoxiribose damage (Romay C, et al. Inflamm. Res. 1998; 47:36-41; Bhat V B, et al. Biochem. Biophys. Res. Commun. 2000; 275:20-25).

It has been proven that C-Phyco significantly inhibits the increase of lipid peroside of rat liver microsomes after ascorbic acid+$Fe^{2+}$ treatment (Romay C, et al. Inflamm. Res. 1998; 47:36-41) or with 2,2' azobis 2-amidinopropane hydrochloride (HAAP). The latter is an initiator of free radical formation (Bhat V B, et al. Biochem. Biophys. Res. Commun. 2000; 275:20-25), indicating that this compound is a good lipid peroxidation inhibitor.

On the other hand, C-Phyco acts as an anti-carcinogenic agent by the inhibition of oxidative damage to DNA mediated by ONOO—, limiting tumor proliferation (Li B, et al. Biomed Pharmacother. 2005; 59: 551-60). Moreover, it was demonstrated that this natural compound inhibits platelet aggregation (Hui-Fen Ch, et al. British Journal of Nutrition. 2006; 95: 435-440).

C-Phyco at a concentration of 1-3 mg/mL, prevents neuron death due to the absence of potassium and serum for 24 h in a culture of brain granulous cells (Rimbau V, et al. Naunyn Schmiedebergs Arch Pharmacol. 2001; 364:96-104).

C-Phyco activity was also examined in a model of brain damage in rats induced by kainic acid (Rimbau V, et al. Neuroscience Letters. 1999; 276: 75-78). The administration of one 100 mg/kg dose of C-Phyco reduced the signs and alterationa evidenced in the treated animals compared to those of the untreated control group. Additionally, it has been demonstrated that C-Phyco inhibits COX-2 through: 1) the assay of the isolated enzyme and (2) the complete blood assay (Reddy C M, et al. Biochem. Biophys. Res. Commun. 2000; 277:599-603).

C-Phyco was able to reduce edemas when administered by the oral route at a dose of 100-200 mg/kg in swollen paw models induced by carragenin and glucose oxidase in mice and rats (Romay Ch, et al. Pharm. Pharmacol. 2000; 52: 367-368; Madhyastha H K, et al. J Cell Mol Med. 2008), and in the mouse-ear inflammation model, induced by araquidonic acid (Romay Ch, et al. Pharm. Pharmacol. 2000; 52: 367-368).

A review summarizes the main studies performed with C-Phyco in different animal models (Curr Protein Pept Sci. 2003 June; 4(3):207-16). Most of the experiments required high doses of C-Phyco (above 100 mg/kg and up to 300 mg/kg) for a therapeutic effect to be observed.

Phycocyanobilin (PCB) is the chromophore of C-Phyco; from the chemical viewpoint it is characterized by the presence of pyrrolic rings without the protein fragment. Interferons (IFNs) were initially discovered as soluble proteins with antiviral activity, and they may be classified in: IFNs type I (IFN alpha and beta) and type II (IFN gamma). Although it is generally considered that IFNs alpha and beta use a common complex receptor, several reports suggest that there are differences in the capacity of IFN alpha and beta to induce certain biological effects. These include the preferential induction of an IFN-specific gene (Rani M R S, et al. J Biol Chem 1996, 271: 22878-22884; Platanias L C, et al. J Biol Chem 1994, 269:17761-17764), inhibiting effects of different growth factors (Rosenblum M G, et al. J Interferon Res 1990, 10: 141-151) and erythropoietic effects (Means R T, et al. Exp Hematol 1996, 24: 204-208). From this, it may be deduced that a biological effect identified for alpha IFN does not have to also be identified for beta IFN and vice-versa.

A possible explanation for different signaling events between alpha and beta IFNs is the existence of phospho-proteins associated to the specific receptor of beta IFN, which seems to be phosphorylated tyrosine, and is associated to receptor 1 of alpha IFN (IFNAR1) (Croze E, et al. J Biol Chem. 1996: 271: 33165-33168; Platanias L C, et al. J Biol Chem. 1996, 271: 23630-23633).

The mechanisms of action of alpha and beta IFN are highly complex. These two cytokines act through different signaling routes. The latter is supported by evidence. Studies carried out in UIA cells, in which JAK kinase TYK2 is absent (Velazquez L, et al. 1992. Cell 70: 313-322) showed that these cells cannot bind with and respond to alpha IFN, but they can do so with beta IFN (Pellegrini S, et al. 1989. Mol Cell Biol 9, 4605-4612). This suggests that the binding sites for alpha IFN require the presence of TYK2. In the case of the binding sites for beta IFN these may be formed in the absence of TYK2.

Clinical Trials (CT) made with alpha IFN in MS have shown poor efficacy (Gilhus E N, World Neurology 1995, 5: 10-12; Sheridan P (ed), Multiple Sclerosis Research in progress 1993-1994. Clinical Trials. International Federation of Multiple Sclerosis Societies, London, 1995, pp. 3-35; Trials with Alferon, human leukocyte interferon alpha. Clinical Trials Monitor, 1997; 4 (12): 4).

Beta IFN is one of the drugs approved by the Food and Drug Administration of the United States (FDA) for MS and reports also reflect its poor effectiveness and its dependence on high doses to achieve an effect (Zaragoza Garcia F et al. Farm Hospit. 2002; 26:294-301).

Additionally, for IFN therapy, secondary effects have been described depending on the dose and administration route. Patients may experiment pseudo-flu reactions such as fever, myalgia, shivering and general discomfort between 24-48 hours after each injection. Necrosis at the injection site takes place in 5% of patients.

On the other hand, one of the main in vivo actions of Interleukin 2 (IL-2) is promoting thymus development and regulatory T cell (Treg) peripheral expansion (cTreg). The loss of the activity of Treg in IL-2 or IL-2Rbeta deficient mice produces severe antigen dependent lymphadenopathy followed by lethal autoimmunity. The presence of IL-2 dependent Treg is based on a number of adoptive transfer and genetic experiments. Recently it has been demonstrated that Treg's have an essential role as brain protective modulators of the post-ischemic inflammatory brain damage (Liesz A et al. Nat Med 200915, 192-199).

Autoimmune disease (such as MS) and brain ischemia are characterized by a relative deficiency of Treg. Therefore, Treg expansion may improve these diseases. IL-2 can produce Treg expansion in vivo providing a potential clinical application of this treatment modality (Liu R. Eur J Immunol. 2010; 40:1577-89).

IL-2 is considered a biological response modifier, which has been used for cancer treatment such as melanoma and kidney cell carcinoma as well as HIV. IL-2 in high dose schedules has been tested, since low dosages do not achieve the desired therapeutic effect.

The high dose Schedule implies the administration of IL-2 by the intravenous route every eight hours, if the patient tolerates it, up to attain 15 doses. This schedule has significant secondary effects, which are reversible in most cases when the treatment is stopped, but due to the severity of some of them, the patients are hospitalized and sometimes require intensive care while receiving the drug.

Another product of special interest is the peptide known as GHRP-6 ("Growth Hormone Releasing Peptide-6"). This peptide, originally described as derived from bowel metaencephalin, showed afterwards an unexpected growth hormone (GH) secretagogue effect in different mammal species—including humans (Bowers C Y, et al. Endocrinology. 1984, 114: 1537-45; Pandya N, et al. J Clin Endocrinol Metab. 1998, 83:1186-9). This molecule has been administered intravenously in humans as a secretagogue agent for differential clinical diagnosis of the different forms of dwarfism (Popovic V, et al. Lancet. 2000; 356:1137-42).

GHRP-6 increases the insulin-like growth factor 1 expression (IGF-1) in the CNS (Frago L. M, et al. Endocrinology 2002, 143:4113-4122). IGF-1 intervenes in certain processes such as: (1) increasing events related to oligodendrocyte maturation (Wilson H. C, et al. Glia 2003, 44:153-165), (2) blocking TNF-alpha dependent apoptosis routes and (3) reducing expression of class I molecules of the main histocompatibility complex (Ito T, et al. Am. J. Pathol 2004, 164:623-634). It has been demonstrated that a GH and IGF-1 secretion reduction is linked to brain ischemic processes, which are more frequent in elderly persons (Frutos M G, et al. Am J Physiol Endocrinol Metab. 2007, 293:E1140-52).

The aging of the GH/IGF-1 axis must be restored with treatments stimulating GH production and secretion. The chronic systemic treatment of adult rats with GHRP-6 increase IGF-1 levels in several brain regions such as hypothalamus and cerebellum. Also, intracellular signaling cascades normally associated with anti-apoptotic actions are activated in theses areas. Sodium glutamate in abnormal high concentrations can provoke neuron hyper-excitation producing cell damage and/or death. GHRP-6 reverts glutamate-induced cell death through reduction of the activation of caspase 7 and 9 (Delgado-Rubín de Célix A, et al. J Neurochem 2006, 99:839-49).

In spite of the success of GH secretagogues synthetic peptides, the persisting problem is that they have to be injected several times a day, they are expensive, having secondary effects and, they probably regulate internal receptors of the signaling cascade, which means that their effect diminish with time. The secondary effects associated to GHRP-6 injections are: cancer, hypotension, congestive heart disease, uncontrolled bleeding, carpian tunnel syndrome, reduction of insulin sensitivity, hypoglycemia, gynecomastia, edema, leukemia in children, ketogenesis and allergic reactions.

Erythropoietin (EPO) acts in an unspecific fashion on components of the "final common cascade" determining the severity or progression of a large number of completely different brain diseases. EPO has anti-apoptotic, anti-inflammatory, anti-oxidant, neurotrophic, angiogenic, and stem cell modulating effects, therefore being able to influence neural plasticity. EPO protecting and regenerative properties have been reported, as well as improvement of cognitive functions in several animal models of neurologic and psychiatric diseases. The "Göttingen-EPO-stroke trial" provided the first promising evidence in humans for a neuroprotective therapy in acute brain diseases. The experimental treatment with EPO to improve cognitive functions in schizophrenic patients represents a new strategy for a chronic brain disease. An exploratory assay in chronic progressive MS, as an example of an inflammatory disease of the nervous system, provided the first positive results of the EPO treatment on the motor and cognitive functions (Ehrenreich H, et al. (2008) J Ren Nutr. 18:146-53). EPO has hematopoietic functions in the brain and other organs, particularly during the development. AsyaloEPO, or low syalic acid EPO, has been identified as a neurotrophic and neuroprotector agent in a broad variety of experimental contexts, from neuron cultures up to in vivo models of brain damage. Different mechanism by which AsyaloEPO produce neuroprotection have been recognized: i) reduction of Sodium glutamate toxicity, ii) induction of the generation of anti-apoptotic neuron factors, iii) reduction of inflammation, iv) reduction of nitric oxide induced damage and, v) direct anti-oxidant effects. Evidence suggests that asyaloEPO can be a new strategy for a large variety of CNS disorders in adults and children, especially as a possible alternative for perinatal asphyxia (S Juul. (2002) Acta Paediatrica 91 s438: 36-42).

The ischemic infarct is associated to a variety of pathophysiological changes that affect neuronal and glial brain tissue. These changes are translated into specific protein release to the peripheral blood. The neuron specific enolase protein, the S100B protein and the specific glial fibrillar protein are possible markers of post-infarction brain damage in humans.

Although EPO and asyaloEPO proteins have been used for brain ischemia and neurodegenerative disease treatment, adverse effects have also been reported associated to their use. EPO therapy and the increase of hematocrit are associated to adverse events such as hypertension and thrombosis. In these cases, the use of drug combinations showing more efficacy is also justified, which could lead to the use of lower doses, other administration routes and reduction of adverse events.

Therefore, finding more potent drugs or combined molecules for CNS ischemic or neurodegenerative damage therapy is needed to reduce adverse events associated to the high doses of the drugs required to achieve the desired effect.

Explanation of the Invention

The present invention solves the above mentioned problem providing chromogenic peptides (PCB-aa) with sequences showed in the List of Sequences and has in their structure a tetra-pyrrolic system. For the first time it is demonstrated that these compounds have properties sustaining their use in prophylaxis or treatment of tissue ischemia or degeneration. In a particular realization they may be used for ischemic and neurodegenerative disease treatment.

The chromogenic or PCB-aa peptides of the invention consist in sequences between 3-6 amino acids of the alpha (α-C-Phyco) and beta (β-C-Phyco) chains of C-Phyco, obtained from their enzymatic digestion.

These peptides are:
SEQ ID NO. 1: $^{79}$MAABLR$^{84}$ (β-C-Phyco);
SEQ ID NO. 2: $^{84}$BAR$^{86}$ (α-C-Phyco);
SEQ ID NO. 3: $^{80}$AABLR$^{84}$ (β-C-Phyco);
SEQ ID NO. 4: $^{82}$BLR$^{84}$ (β-C-Phyco);
SEQ ID NO. 5: $^{81}$ABLR$^{84}$ (β-C-Phyco)

Where B (in bold) is a cysteine covalently bound to phycocyanobilin (PCB). Also, the objective of the present invention is a pharmaceutical composition comprising at least one peptide identified as SEQ ID NO. 1-5 and pharmaceutically acceptable excipients.

A novelty of the invention consists in demonstrating a neuroprotector and neuroregenerator effect which is higher than that of the chromogenic peptides and PCB, with respect to C-Phyco, showing protection from the damage induced by Sodium glutamate, a mechanism resembling brain ischemia, in the cell line PC12 and in animal models of brain ischemia and MS.

The PCB-aa land the PCB peptides showed protection in molar concentrations 25 times lower for PCB-aa and 10 times lower for PCB (2 µM of PCB-aa and 5 µM of PCB protect 100% of the cells submitted to the damage), while 50 µM of C-Phyco to protect around 75% of the cells were needed.

Additionally, in a particular realization, a reduction of the volume of the infarction in the brain ischemia reperfusion model I/R in Mongolian Gerbils was demonstrated, when the animals were treated with PCB-aa and PCB. The results show a higher effectiveness for PCB-aa (49.2%) respect to PCB (43.1%).

Therefore, the objective of the present invention is also the use of a selected compound of the group composed by the peptides identified as SEQ ID NO. 1-SEQ ID NO. 5, named PCB-aa for short, and PCB for manufacturing a drug useful for ischemia or tissue degeneration treatment. In a particular realization, said compound is used in ischemic, inflammatory or neurodegenerative damaging CNS disease prophylaxis or treatment.

Another aspect of the invention is that it provides a method for ischemia or tissue degeneration treatment or prophylaxis characterized by its administration as a pharmaceutical composition comprising a selected compound from the group composed by the peptides identified as SEQ ID NO. 1-SEQ ID NO. 5 and PCB to a subject needing it. In a particular realization, the invention method is characterized because the ischemia or tissue degeneration produces CNS diseases that progress with ischemic, inflammatory or neurodegenerative damage.

In another materialization, the invention provides a pharmaceutical combination comprising a first component, selected among the Group composed by the peptides identified as SEQ ID NO. 1-SEQ ID NO. 5 and phycocyanobilin, and a second component, selected from the group composed by type I interferons, including alpha (IFN-a) and beta (IFN-b) interferons, Interleukin-2 (IL-2), Erytropoitin (EPO), asyaloEPO and the secretagogue peptide of the human GH (GHRP-6).

The synergic effect of the active components, referred to their neuroprotective and/or neuroregenerative properties, justifies their use in brain ischemia of different origins and in neurodegenerative diseases such as MS, Alzheimer's disease, lateral amyotrophic sclerosis, Spinal-cerebellar ataxia, Huntington's disease and Parkinson's disease.

Although alpha and beta IFNs are type I IFNs and use a complex common receptor, a number of observations suggest that there are differences in the properties of alpha and beta IFNs to induce certain biological effects.

In a particular realization the evaluation of the PCB-aa/IFN-a and PCB/IFN-a combinations were performed in a prophylactic schedule in the experimental autoimmune encephalomyelitis (EAE) model demonstrating a synergic effect of the mentioned combinations in respect to the independent active principles, regarding the prevention of the development of the disease.

In another particular realization, the PCB-aa and PCB combination with IFN-a and IFN-b were evaluated comparing them to their independent active principles, administered at doses of 3.375 mg/Kg of PCB-aa, 750 µg/Kg of PCB and 500 ng/Kg for both IFNs, showing a relative effectiveness regarding the decrease of the volume of the brain infarction of 83.3% and 89.3%, for the combinations of IFN-a with PCB and PCB-aa, respectively; and 87.0% and 93.6%, for the combinations of IFN-b with PCB and PCB-aa, respectively, which are higher than the active principles separately in the model of brain I/R in Mongolian gerbils.

Additionally, in another particular realization, the combinations PCB-aa/IFN-b and PCB/IFN-b were evaluated, which were administered at a daily dose of 3.375 mg/Kg of PCB-aa/Kg, 750 µg/Kg of PCB and 6 doses of 500 ng/Kg of IFN-b.

Results showed a relative effectiveness in the decrease of clinical symptoms that is greater than that of the active principles separately in the EAE model. Hence, a therapeutic effect in the EAE animal model was also demonstrated.

Other realizations included the evaluations of the combinations of PCB-aa/IFN-b and PCB/IFN-b as a pharmaceutical combination administered by different routes (intraperitoneally, nasal, oral and rectal) in the EAE model, demonstrating a similar pharmacological effect in respect to clinical signs. The compounds forming part of the mentioned pharmaceutical combinations may be applied simultaneously or separately in the same individual during the course of a single treatment. The pharmaceutical combinations referred to in this invention may be for parenteral, nasal, oral or rectal administration; with appropriate excipients for these routes.

In another particular realization, the effect of PCB-aa, PCB and IL-2 in brain ischemia was evaluated. The combination PCB-aa/IL-2 and PCB/IL-2 had a synergic effect regarding the reduction of the volume of the brain infarct in respect to the active components independently (49.2% effectiveness for PCB-aa, 43.1% effectiveness for PCB, 25.8% for IL-2 and 84.3% for the combination of PCB-aa/IL-2 and 74.5% for the combination PCB/IL-2) in the model of brain ischemia in Mongolian gerbils.

On the other hand, the evaluation of the combination PCB/GHRP-6 and the independent active principles was performed, administering them intraperitoneally in the brain I/R animal model in Mongolian gerbils. From the morphometric point of view a synergic effect was observed with the combination, which had a value of 85% effectiveness with respect to 35.8% for PCB and 36.1% for GHRP-6).

Another novelty of this invention consisted of the synergic effect in relation to the reduction of the infarct volume demonstrated for the combinations PCB-aa/EPO and PCB-aa/asyaloEPO; compared to the separate components (49.2% effectiveness for PCB-aa, 36.9% for EPO, 39.4% for asyaloEPO, 87.7% for the combination PCB/EPO, 90.5% for the combination PCB/asyaloEPO, 91.7% of the combination PCB-aa/EPO and 94.5% for the combination PCB-aa/asyaloEPO). The former justifies the use of said combinations for the treatment of CNS diseases that progress, or are the result, of ischemic damage.

The components forming the therapeutic combination of the invention can be administered simultaneously or sequentially to the same individual during the course of a medical treatment.

Also objective of the invention is the use of the pharmaceutical combination comprising a first component, selected from the group composed by the peptides identified as SEQ ID NO. 1-SEQ ID NO. 5 and phycocyanobilin, and a second component, selected from the group composed by type I IFNs, including alpha (IFN-a) and beta (IFN-b) IFNs, Interleukin-2 (IL-2), Erythropoietin (EPO), asyaloEPO and the human GH secretagogue peptide (GHRP-6), for manufacturing a medicament for prophylaxis or treatment of CNS diseases of ischemic, inflammatory or neurodegenerative origin. In one aspect of the invention the said medicament protects the damaged brain parenchyma as a consequence of acute or chronic diseases.

The invention also covers a method for the prophylaxis or treatment of CNS diseases of ischemic, inflammatory or neurodegenerative origin, which is characterized through the administration of a pharmaceutical combination comprising:

a first component, selected from the group formed by peptides identified as SEQ ID NO. 1-SEQ ID NO. 5 and phycocyanobilin; and a second component selected from the group formed by type I Interferons that include alpha interferon (IFN-a) and beta interferon (IFN-b), Interleukin-2 (IL-2), Erythropoietin (EPO), asyaloEPO and the secretagogue peptide of the human growth hormone (GHRP-6) to a subject needing it. This method is characterized because the components forming the combination may be administered simultaneously or sequentially to the same subject in the course of a medical treatment. In a particular intervention this treatment was applied to brain ischemia of different origins, MS, Alzheimer's Disease, Lateral Amyotrophic Sclerosis, Spinal-Cerebellar Ataxia, Huntington's Disease and Parkinson's Disease.

BRIEF DESCRIPTION OF THE FIGURES

FIG. 2. In vitro study of the neuroprotector effect of C-Phycocyanin (C-Phyco) (A) and of PCB and PCB-aa (B) against the Sodium glutamate (50 mM) induced damage in the neuronal line PC12. The symbols indicate the presence (+), absence (−) or concentrations of the respective compounds in the culture medium. Different letters indicate statistically significant difference, according to ANOVA followed by the Newman-Keuls multiple comparison test, p<0.05. The values presented in the graphs are the means±standard error of the mean (MSE).

DETAILED EXPOSITION OF THE REALIZATION MODES/REALIZATION EXAMPLES

Example 1

Mass Spectrometry of Phycocyanobilin (PCB) Obtained by Metanolic Treatment and of the Chromogenic Peptides (PCB-aa)

Figure 1:
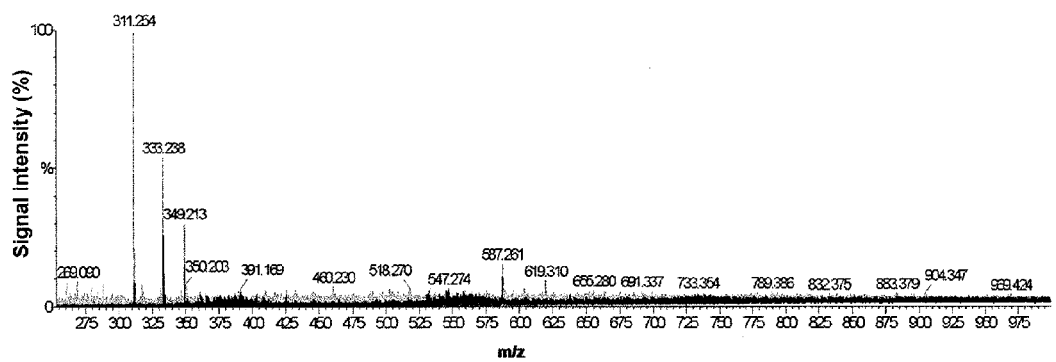
FIG. 1. Characterization by mass spectrometry of PCB obtained by metanolic treatment (A) and the chromogenic peptides obtained by trypsin digestion, defined together as PCB-aa, B: SEQ ID NO. 1; C: SEQ ID NO. 2; D: SEQ ID NO. 3-5.
Figure 1:
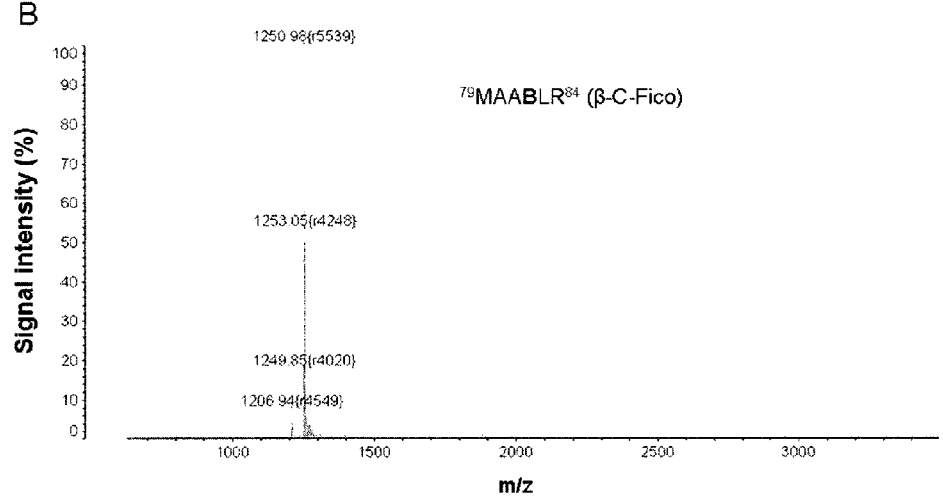
Figure 1:
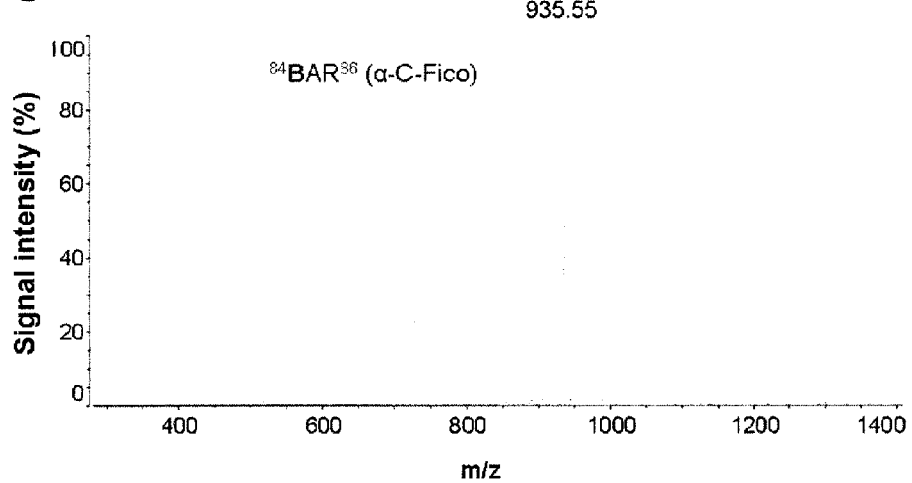

FIG. 1A shows the m/z signal 587.26 corresponding to the chromophore PCB, obtained by differential ultrafiltration of the C-Phyco metanolic extract.

FIGS. 1B, C and D show the mass spectrometry pattern of PCB-aa obtained by trypsin digestion of C-Phyco.

Example 2

Neuroprotector Effect of C-Phyco, PCB and PCB-aa Against the Sodium Glutamate Induced Damage in the PC12 Cell Line PC12 cells ($1.5 \times 10^4$ cells/well) were pretreated with C-Phyco (25, 50 µM) or PCB (0.5; 1; 5 µM) or PCB-aa (0.25; 1; 2 µM), during 24 h, and then submitted to co-incubation with 50 µM Sodium glutamate together with the corresponding product (different doses) for 4 h. The cell viability was measured by the (3-(4,5-Dimetiltiazol-2-il)-2,5-difeniltetrazolium bromide method (MTT) and the percentage with respect to the control was reported, as shown in FIG. 2. It can be observed that to attain similar cell viability to that of C-Phyco lower concentrations of PCB and PCB-aa were needed. The PCB-aa (peptide 1) concentrations that achieved a similar effect to PCB and C-Phyco were even lower in respect to the said compounds.

Example 3

Demonstration of Neuroprotector and/or Neuroregenerator Properties of PCB-aa Peptides, by Means of the Infarct Volume Reduction, in the Mongolian Gerbil I/R Model The animals were treated with saline solution or with an accumulative dose of the PCB-aa peptides (3.375 mg/kg of each one), by intraperitoneal route for 30 min, 3, 6 and 12 h after the ischemic event.

The effectiveness percentage of each treatment was calculated according to the following formula: effectiveness %=(1−Vi/VI/R)×100. Vi: infarct volume of the ischemic group treated with the corresponding product; VI/R: volume of the infarct of the ischemic group treated with saline solution.

Figure 3:
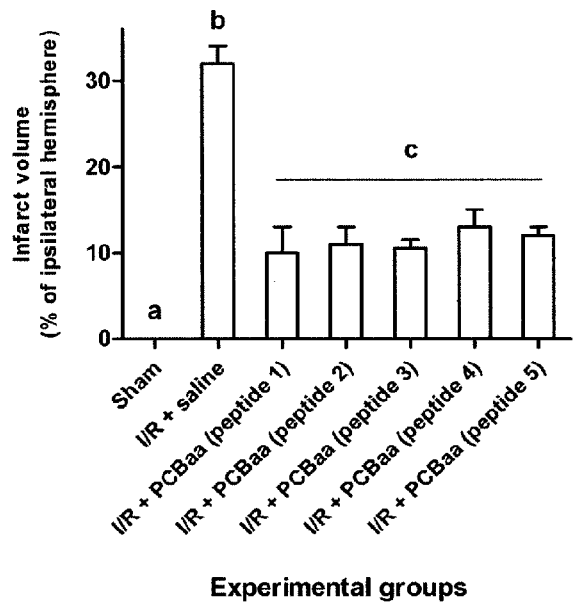
FIG. 3. PCB-aa (peptides 1 to 5) therapeutic treatment effect on the brain infarct volume, 24 h after the transient occlusion (10 min) of the common carotid arteries (CCA) in Mongolian gerbils. Different letters indicate statistically significant difference, according ANOVA followed by the Newman-Keuls multiple comparisons test, p<0.05. The values are presented in the graphs as the means±MSE.

As may be observed in FIG. 3, the animals treated with the chromogenic peptides (PCB-aa) consisting in the SEQ ID NO: 1 to the SEQ ID NO: 5, showed a significant reduction of the infarct volume with respect to the ischemic group treated with saline solution.

Example 4

Figure 4:
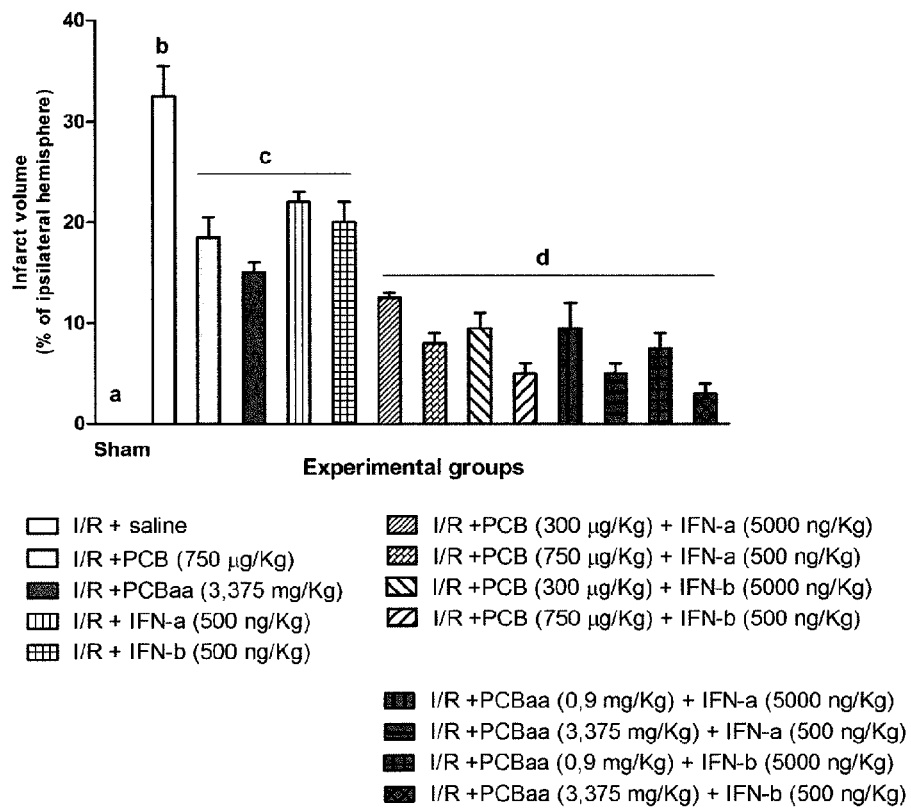
FIG. 4. Effect of therapeutic treatment with PCB, PCB-aa (peptide 1), IFN-a and IFN-b and the PCB/IFN-a, PCB/IFN-b, PCB-aa/IFN-a and PCB-aa/IFN-b combinations on the brain infarct volume, 24 h after the transient (10 min) occlusion of the CCA in Mongolian gerbils. Different letters indicate statistically significant difference regarding the I/R group+saline, p<0.05. The values are presented in the graphs as the means±MSE.

Effect of the Combinations PCB/IFN-a, PCB-aa (Peptide 1)/IFN-a, PCB/IFN-b and PCB-aa (Peptide 1)/IFN-b in the Bilateral Ischemia-Reperfusion Model in Gerbils The animals were treated with saline solution (by intraperitoneal route) or with the individual compounds at a dose of PCB (750 µg/Kg, intraperitoneal route), or PCB-aa (peptide 1) (3.375 mg/kg), IFN-a and IFN-b (500 ng/Kg, subcutaneous route) or with the combinations PCB/IFN-a, PCB/IFN-b, PCB-aa (peptide 1)/IFN-a and PCB-aa (peptide 1)/IFN-b according to the doses indicated in FIG. 4 by 30 min, 3, 6 and 12 h after the ischemic event. The percentage of effectiveness was calculated as described in Example 3.

The reduction of the brain infarct volume, by groups, evidences the effectiveness of the evaluated treatments (FIG. 4), observing a reduction of the infarct index in the group treated with PCB with an effectiveness of 43.1%; with PCB-aa (peptide 1) of 49.2%; in the group treated with IFN-a of 35.4%; with IFN-b of 37.0%; in the group treated with PCB/IFN-a of 83.3%; PCB-aa (peptide 1)/IFN-a of 89.3%; PCB/IFN-b of 87.0%; and PCB-aa (peptide 1)/IFN-b of 93.6%; evidencing a synergic effect of both active principles in the animals treated with the combination.

Example 5

Demonstration of the Pharmacological Effect of the PCB/IFN-a and PCB-aa (Peptide 1)/IFN-a Combinations with Respect to the Active Principles Independently, Referred to the Clinical Signs in the EAE Model On the other hand, the evaluation of the combinations PCB/IFN-a and PCB-aa (peptide 1)/IFN-a was performed in the prophylactic schedule, in the EAE model (Table 1), where a synergic effect of the said combination regarding the prevention of the development of the disease at the doses declared formerly, was demonstrated.

TABLE 1

Evaluation of the PCB-aa (peptide 1)/IFN-a and PCB/IFN-a combinations and their active principles independently in the prophylactic schedule in the EAE model.

| Groups | Incidence (%) | Clinical Index | | |
|---|---|---|---|---|
| | | Starting Day (Mean ± SD) | Clinical score (Mean ± SD) | Days of the disease |
| Control | 0 | 0 | 0 | 0 |
| PCB-aa (peptide 1) (3.375 mg/Kg) | 75 | 9.5 ± 0.2 | 1.23 ± 1.1 | 7.2 ± 0.3 |
| PCB (750 µg/Kg) | 70 | 10.5 ± 0.5 | 1.37 ± 1.7 | 8.5 ± 0.1 |
| IFN-a (500 ng/Kg) | 60 | 10.7 ± 0.3 | 1.5 ± 1.6 | 7.3 ± 0.7 |
| PCB-aa (peptide 1) (3.375 mg/Kg) + IFN-a (500 ng/Kg) | 0 | 0 | 0 | 0 |
| PCB-aa (peptide 1) (0.9 mg/Kg) + IFN-a (5000 ng/Kg) | 12 | 11.3 ± 0.2 | 0.5 ± 0.1 | 4.5 ± 0.5 |
| PCB (750 µg/Kg) + IFN-a (500 ng/Kg) | 10 | 12.4 ± 0.2 | 0.9 ± 0.1 | 5.4 ± 0.6 |
| PCB (300 µg/Kg) + IFN-a (5000 ng/Kg) | 15 | 12.8 ± 0.3 | 1.12 ± 0.5 | 6.6 ± 0.2 |
| EAE | 100 | 10.2 ± 0.7 | 2.7 ± 0.4 | 15.2 ± 1.1 |

As shown in Table 1, the combinations with different doses of PCB/IFN-a and PCB-aa (peptide 1)/IFN-a provide protection of between 85% and 100% of the animals induced to develop EAE, respectively.

Example 6

Demonstration of the Pharmacological Effect of the Combinations PCB/IFN-b and PCB-aa (Peptide 1)/IFN-b in Relation to the Active Principles Independently, Referred to the Clinical Signs in the EAE Model To demonstrate that the pharmacological effect of the combinations PCB/IFNb and PCB-aa (peptide 1)/IFN-b, in the prophylactic (Table 2) as well as in the therapeutic schedule (FIG. 5), in relation to the reduction of the clinical signs in C57BL6 mice the following individual compounds were used: PCB (750 µg/kg, intraperitoneal route), PCB-aa (3.375 mg/kg, intraperitoneal route) administered daily for 15 days and IFNb (500 ng/Kg, subcutaneous route) 6 doses, 3 times a week, or their combinations according to the doses indicated in Table 2 were used.

The percentage of effectiveness of each treatment was calculated according to the following formula: % of effectiveness=(1−$AC_t$/$AC_{EAE}$)×100. $AC_t$: area under the curve of the group treated with the corresponding product; $AC_{EAE}$: area under the curve of the EAE group.

In the prophylactic schedule the treatment was performed 15 days before EAE induction and in the therapeutic schedule starting from the beginning of the clinical signs. The control group corresponds to healthy animals that did not receive any treatment.

Table 2 shows the results obtained in the prophylactic schedule, where the combinations PCB/IFN-b and PCB-aa (peptide 1)/IFN-b protected from 90% to 100% of the animals from EAE development respectively. Hence, a synergic effect was observed regarding the independent active principles.

TABLE 2

Evaluation of the combinations PCB-aa (peptide 1)/IFN-b and PCB/IFN-b, and their active principles independently, in the EAE prophylactic model.

| Groups | Incidence (%) | Starting day (Mean ± DS) | Clinical index Clinical score (Mean ± SD) | Days of the disease |
|---|---|---|---|---|
| Control | 0 | 0 | 0 | 0 |
| PCB-aa (peptide 1) (3.375 mg/Kg) | 70 | 9.5 ± 0.2 | 1.23 ± 1.1 | 7.2 ± 0.3 |
| PCB (750 µg/Kg) | 60 | 12.3 ± 0.1 | 1.55 ± 0.3 | 7.3 ± 0.4 |
| IFN-b (500 ng/Kg) | 70 | 12.6 ± 0.5 | 1.4 ± 0.2 | 7.1 ± 0.3 |
| PCB-aa (peptide 1) (3.375 mg/Kg) + IFN-b (500 ng/Kg) | 0 | 0 | 0 | 0 |
| PCB-aa (peptide 1) (0.9 mg/Kg) + IFN-a (5000 ng/Kg) | 10 | 12.1 ± 0.1 | 0.4 ± 0.1 | 4.2 ± 0.2 |
| PCB 750 µg/Kg) + IFN-b (500 ng/Kg) | 5 | 12.5 ± 0.1 | 1.1 ± 0.1 | 4.4 ± 0.3 |
| PCB (300 µg/Kg) + IFN-b (5000 ng/Kg) | 10 | 12.5 ± 0.2 | 1.21 ± 0.4 | 6.2 ± 0.1 |
| EAE | 100 | 10.1 ± 0.3 | 2.3 ± 0.6 | 1.2 ± 1.1 |

Figure 5:
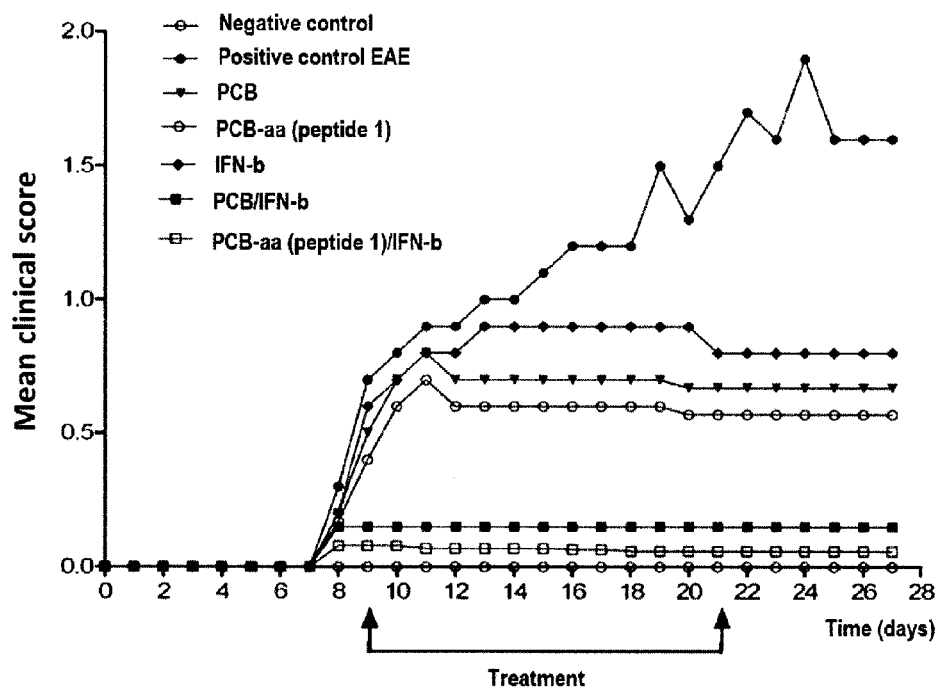
FIG. 5. Effect of the PCB-aa (peptide 1)/IFN-b, PCB/IFN-b combinations and their independent active principles on the clinical course of EAE in C57BL6 mice. The values presented in the graphs are the means of the clinical index of each group.

FIG. 5 shows a reduction of the clinical signs that is greater than the reduction obtained with the active principles independently, PCB (750 µg/kg, intraperitoneal route), PCB-aa (3.375 mg/kg, intraperitoneal route), IFN-b (500 ng/Kg, subcutaneous route), evidencing also in the therapeutic schedule a synergic effect in the group treated with the combinations in the EAE model, PCB (750 µg/kg)/IFN-b (500 ng/Kg) or PCB-aa (3.375 mg/kg)/IFN-b (500 ng/Kg), with 87.7% effectiveness for the combination PCB/IFN-b; 94.5% for the combination PCB-aa/IFN-b; 46.1% for PCB; 53.9% for PCB-aa and 34.8% for IFN beta.

Example 7

Demonstration of the Therapeutical Effect of the Combination PCB-Aa (Peptide 1)/IFNb by Different Routes in the EAE Model The animals of the EAE group received a daily administration of saline solution by the intraperitoneal route. The mice treated with the combination PCB-aa (peptide 1)/IFN-b (PCB-aa 3.375 mg/kg+500 ng de IFN-b/Kg) were divided into different groups, according to the administration route: intraperitoneal, oral, nasal and rectal. The therapeutic schedule was followed for 15 consecutive days, from day 9 and up to day 24 after immunization. The control group corresponds to the healthy mice that did not receive any treatment. The clinical evaluation was performed day 27 after immunization.

Figure 6:
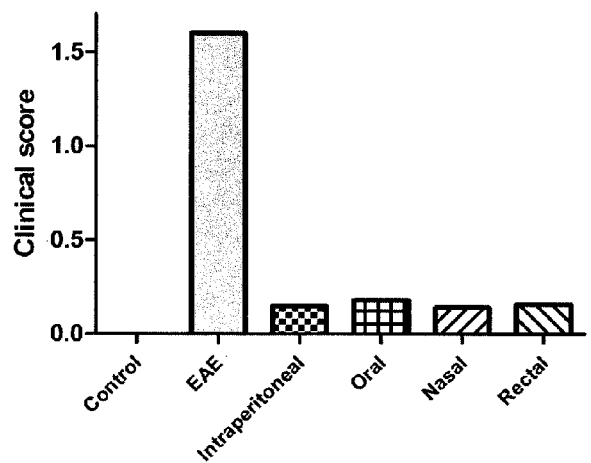
FIG. 6. Effect of the PCB-aa (peptide 1)/IFN-b combination administered by different routes: intraperitoneally, nasal, oral y rectal on the clinical index of sick EAE C57BL6 mice. The values presented in the graphs are the means of the clinical index of each group.

As evidenced in FIG. 6, statistically significant differences were not detected between the different routes evaluated (intraperitoneal, nasal, oral and rectal), which indicates that they can be used with equal effectiveness.

Example 8

Figure 7:
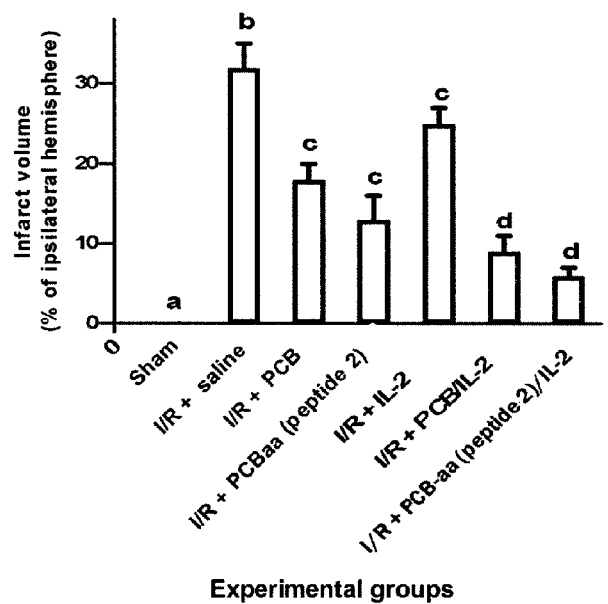
FIG. 7. Therapeutic effect with PCB, PCB-aa (peptide 2), IL-2, or the combinations PCB/IL-2 and PCB-aa (peptide 2)/IL-2, on the volume of the brain infarct, 24 h after the transient (10 min) occlusion of the CCA in Mongolian gerbils. Different letters indicate significant differences with respect to the I/R+saline group, *p<0.05. The values presented in graphs are means±MSE FIG. 8. Morphometric evaluation of the therapeutic effect with PCB-aa (peptide 3), the GHRP-6 peptide, or its combination in Mongolian gerbils submitted to transient (10 min) occlusion of CCA. A: representative images (4× magnification) of the left hippocampus of animals that underwent fake surgery (sham), or treated with saline solution, or with PCB-aa (peptide 3) and GHRP-6 (6.25 µg/kg, intraperitoneal route), or with PCB-aa (peptide 3)/GHRP-6 (maintaining the corresponding doses and administration routes) for 30 min, 3, 6 and 12 h after the ischemic event. B: bilateral cell count performed in the C2, CA3 and CA4 regions of both hippocampi for each experimental group. Different letters indicate significant differences with respect to the I/R+saline group, *p<0.05. The values presented in the graphs are means±MSE FIG. 9. Effect of therapeutic treatment with PCB, PCB-aa (peptide 4), EPO, asyaloEPO, or their respective combinations PCB/EPO, PCB/asyaloEPO, PCB-aa (peptide 4)/EPO and PCB-aa (peptide 5)/asyaloEPO on the brain infarct volume, 24 h after transient occlusion (10 min) of CCA in Mongolian gerbils. Different letters indicate significant differences with respect to the I/R+saline group, p<0.05. The values presented in graphs are means±MSE

Neuroprotector and/or Neuroregenerator Effects of the Combination PCB/IL-2 and PCB-Aa (Peptide 2)/IL-2 in the Bilateral I/R Model in Gerbils The animals were treated with saline solution (by intraperitoneal route) or with an accumulative dose of PCB (750 µg/Kg, by intraperitoneal route), PCB-aa (peptide 2) (3.375 mg/kg), IL-2 (100 ng/Kg, subcutaneous route) or with PCB/IL-2 and PCB-aa (peptide 2)/IL-2 (maintaining the corresponding dose and administration route) for 30 min, 3, 6 and 12 h after the ischemic event. In FIG. 7 a reduction of the infarct volume by group can be observed.

The percentage of effectiveness of each treatment was calculated as described in Example 3, which was 43.1% for PCB; 49.2% for PCB-aa (peptide 2); 25.8% for IL-2; 74.5% for the PCB/IL-2 combination; and 84.3% for PCB-aa (peptide 2)/IL-2), which evidence a synergic effect of both active principles in the animals treated with the combination.

Example 9

Therapeutic Effect of the PCB/GHRP-6 Combination and its Active Principles Independently, in the Bilateral Ischemia-Reperfusion Model in Gerbils The morphometric evaluations of the therapeutic treatment with PCB-aa (peptide 3), the GHRP-6 peptide or its combinations were tested in Mongolian gerbils submitted to transient (10 min) CCAs occlusion. Accumulative doses of PCB-aa (peptide 3) (750 µg/Kg, by intraperitoneal route), GHRP-6 (6.25 µg/kg, intraperitoneal route), or with PCB-aa (peptide 3)/GHRP-6 (maintaining the corresponding dose and administration route) for 30 min, 3, 6 and 12 h after the ischemic event were evaluated. The bilateral cell count was performed in the C2, CA3 and CA4 regions for each experimental group and it was expressed in percentage with respect to the sham (negative or fake surgery) group. The results showed that in the animals of the I/R group, there was an almost complete loss of the cell line which encompasses practically all hippocampus zones (CA2, CA3, CA4).

Figure 8:
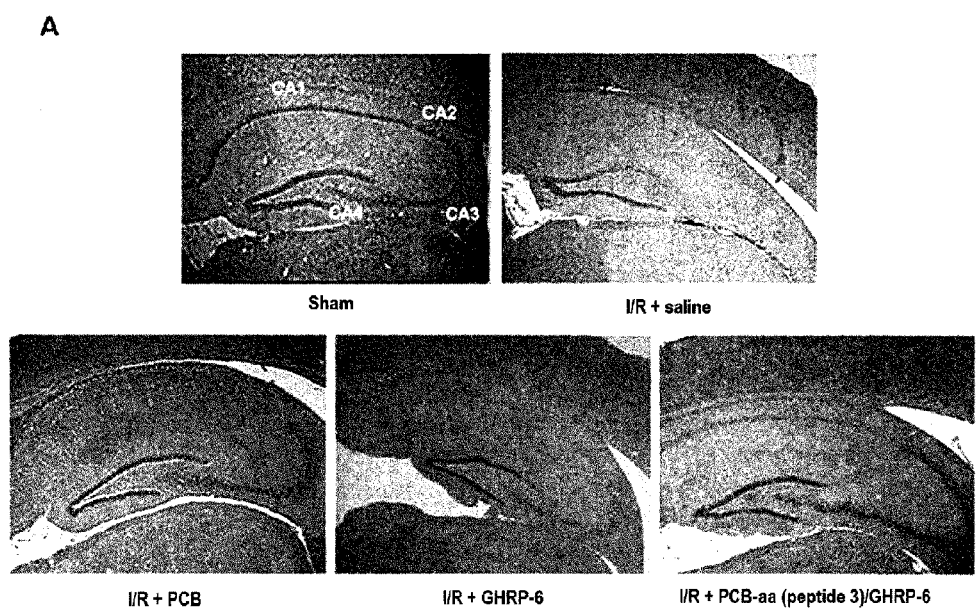

A synergic effect was observed in the group treated with the PCB-aa combination (peptide 3)/GHRP-6 (85% effectiveness), in relation to the independent active principles with an effectiveness of 35.8% for the PCB-aa (peptide 3) and 36.1% for GHRP-6 (FIG. 8).

Example 10

Therapeutic Effect of the PCB/EPO, PCB-Aa (Peptide 4)/EPO, PCB/asyaloEPO and PCB-Aa (Peptide 5)/asyaloEPO Combinations and their Independent Active Principles in the Bilateral I/R Model in Gerbils The animals were treated with a saline solution (through the intraperitoneal route) or with an accumulative dose of PCB (750 µg/Kg, by the intraperitoneal route), PCB-aa (peptide 4) 3.375 mg/kg, EPO (500 U/Kg, through the intraperitoneal route), asyaloEPO (200 U/Kg, through the nasal route) or with PCB/EPO or PCB-aa (peptide 4)/EPO, PCB/asyaloEPO and PCB-aa (peptide 5)/asyaloEPO (maintaining the dose and the corresponding administration route) for 30 min, 3, 6 and 12 h after the ischemic event.

The evaluation of the therapeutic effect of the combinations and their independent components was carried out. The percentage of effectiveness of each treatment was calculated as described in Example 3.

A decrease of the brain infarct volume per group was observed, which evidenced the effectiveness of the treatments evaluated (FIG. 9), with a reduction of the infarct volume in the group treated with PCB of 43.1% effectiveness; PCB-aa (peptide 4) of 49.2%; EPO of 36.9%; asyaloEPO of 39.4%; and even greater in the groups treated with PCB/EPO (87.7% effectiveness), PCB/asyaloEPO (90.5% effectiveness), PCB-aa (peptide 4)/EPO (91.7%) and PCB-aa (peptide 5)/asyaloEPO (94.5%), which shows a synergic effect of the active principles in the combinations.

INCORPORATION OF SEQUENCE LISTING

Incorporated herein by reference in its entirety is the Sequence Listing for the above-identified Application. The Sequence Listing is disclosed on a computer-readable text file titled "Sequence_Listing_976-86PCTUS.txt", created on Dec. 18 2013. The sequence.txt file is 1.57. KB in size.

The invention claimed is:

1. A pharmaceutical combination characterized by its components having a synergic effect and comprising a first component consisting of (i) any of the chromogenic peptides identified as SEQ ID NO:2-SEQ ID NO:5 (PCB-aa) or (ii) phycocyanobilin (PCB), and a second component selected from the group consisting of interferon beta, Interleukin-2 (IL-2), Erythropoietin (EPO), asyaloEPO and Peptide secretagogue of the human growth hormone (GHRP-6).

2. The combination according to claim 1 wherein said first component is present in an amount of 0.9-3.375 mg of any of the peptides identified as SEQ ID NO:2 to SEQ ID NO:5 per Kg of weight of a treated patient, or 300-750 μg of phycocyanobilin per Kg of weight of a treated patient and the second component is present in a range of 500-5000 ng of the interferon beta.

3. A method for the prophylaxis or the treatment of ischemia or tissue degeneration, said method comprising administering the pharmaceutical combination of claim 1 to a subject in need thereof.

4. The method according to claim 3 wherein ischemia or tissue degeneration produces diseases of the CNS that progress with ischemic, or neurodegenerative damage.

5. A method for the prophylaxis or treatment of ischemic or neurodegenerative CNS diseases, said method comprising administering the pharmaceutical combination of claim 1 to a subject in need thereof.

6. Method according to claim 5 wherein said combination protects the brain parenchyma damaged as a consequence of acute or chronic diseases.

7. The method according to claim 5 wherein the combination is administered simultaneously to the same subject during the course of a medical treatment in CNS diseases selected from the group consisting of brain ischemia, multiple sclerosis, Alzheimer's disease, Amyotrophic Lateral Sclerosis, Spinocerebellar ataxia, Huntington's disease and Parkinson's disease.

* * * * *